United States Patent [19]
Gettig et al.

[11] Patent Number: 5,148,004
[45] Date of Patent: Sep. 15, 1992

[54] CONTAMINATED NEEDLE STERILIZER

[75] Inventors: William A. Gettig; Larry E. Shook, both of Millheim, Pa.

[73] Assignee: Gettig Technologies, Inc., Spring Mills, Pa.

[21] Appl. No.: 578,283

[22] Filed: Sep. 6, 1990

[51] Int. Cl.⁵ .............................................. H05B 3/64
[52] U.S. Cl. ..................................... 219/390; 219/521
[58] Field of Search ............... 219/390, 385, 386, 387, 219/521

[56] References Cited
U.S. PATENT DOCUMENTS 3,436,171  4/1969  Weichselbaum ................. 219/390
4,568,426  2/1986  Orlando ........................... 219/390

Primary Examiner—Teresa J. Walberg
Attorney, Agent, or Firm—Richard C. Litman; John R. Wenzel

[57] ABSTRACT

A sterilizing apparatus and method for contaminated syringe needles includes an elongated heating tube having a central bore capable of receiving only the needle of a syringe assembly and which is heated by electrical resistance material surrounding the tube. Precise regulation over the interval and level of heating of the tube is provided through a power controller associated with logic circuitry, switches and a series of timers sequentially initiated. In this manner, should a fault in the apparatus exist and the temperature within the heating tube not reach at least 900 degrees F. within the duration of the cycle of a first one of the timers, the power controller interrupts passage of current to the heating tube. On the other hand, when this temperature is achieved during the time cycle of the first timer, a second timer is initiated and allows continued passage of current to the heating tube for a prescribed interval calculated to achieve the desired sterilization. The concentrated heat as applied to the air within the restrictive tube bore additonally physically renders the sterilized needle un-usable as it will have been annealed and this fact will be apparent from its blackened appearance.

9 Claims, 3 Drawing Sheets

CONTAMINATED NEEDLE STERILIZER

FIELD OF THE INVENTION

This invention relates generally, to needle treatment and more particularly, to an improved method and apparatus for destroying bioburden existing on used hypodermic needles.

BACKGROUND OF THE INVENTION

The necessity of providing means for properly accommodating used hypodermic needles is well recognized and has been addressed since the advent of the administration of medicaments by such devices. For decades, hypodermic syringes and the related cannulas or needles, were constructed with the intent of re-using each of these members repeatedly. Thus, the syringe assemblies were all manufactured of glass and after each use, were suitably sterilized along with the stainless steel needles, such as by autoclaving. Personnel utilizing these re-usable syringes accordingly were attuned to accounting for the soiled device after administering the medication, since the syringes were always destined for usually prompt autoclaving so that they would be available for re-use. For several years now, the majority of medical injections have been administered by means of single-use, throw-away syringes and wherein the packaged, sterilized syringe is constructed of plastics. The same type of stainless steel needles are now used but even these are treated as a single-use, throw-away item, often included in the same package as the syringe.

With the ever increasing threat of becoming exposed or infected, as with the AIDS virus, the more prevalent infectious hepatitis or other diseases, medical personnel as well as their patients are very concerned about the possibility of accidentally being infected through carelessness associated with the handling of used hypodermic syringe assemblies and most especially, the soiled needle. Whether using the older, re-usable glass syringes or the currently popular single-use plastics syringes, the fact remains that as long as bioburden remains on or within a used needle, anyone subsequently handling or being exposed to the device will be at risk. This danger may occur five minutes after use of the syringe, as in the septic tray used to remove the syringe from the hospital room or doctor's office or, in the case of the single-use devices could occur five days or weeks later at any point in the chain of the medical waste disposal route.

Even with the proliferation of no-stick needle devices to ward off the likelihood of accidental skin pricks from used needles, such devices at best usually only mask the problem since any bioburden will still exist on or in the needle and therefore continues to present a threat throughout the usual currently employed disposal precedures.

Obviously, a need exists for a method and apparatus for quickly, safely and positively sterilizing contaminated syringe needles and which is employed at the point of use, even before being placed in a septic tray, waste basket or the like.

DESCRIPTION OF THE RELATED ART

An early example of the sterilizing of cannulas will be found in the patent of Boehm, U.S. Pat. No. 1,129,271 and which suggests the use of electric heating but wherein oxidation is avoided so that the cannula may be reused. U.S. Pat. No. 2,166,284 issued to Brandt teaches the sterilizing of syringes by immersion within an electrically heated liquid. More recently, efforts have been made to physically destroy used syringe needles, as by bending or breaking, although most of these devices do not necessarily eliminate any bioburden that is present. Examples of such devices will be found in U.S. Pat. Nos. 3,893,608, 4,332,323 and 4,786,280. The present proposal is intended to provide an improvement over any known method or apparatus for sterilizing contaminated needles.

SUMMARY OF THE INVENTION

By the present invention, an improved apparatus is provided for accomplishing the rapid and positive sterilization of contaminated needles in a manner that, in a relatively short period of time not only destroys any bioburden in or on the needle but also, renders the needle un-usable for further injections. The instant treatment involves the insertion of the needle into a cavity of a compact apparatus after which, the subsequent manipulation of two or more switches initiates a series of timed sequences resulting in the annealing of the needle and destroying of bioburden existing in or on the needle. Not only is the needle decontaminated so that the used syringe and needle may be safely disposed of in the conventional manner, but the same heat of sterilization has annealed the needle and colored it black. These latter physical and visual properties not only render the needle un-usable due to its softness but also provides a clearly observed visual indication that the needle has been altered in some manner, thereby discouraging a drug addict for example, from attempting to re-use the syringe should they come upon the discarded article.

To be effective, any system of the present type must be relatively economical so that it may be employed at each and every point of use and its operation should be quick and simple. By the instant invention, a compact, inexpensive apparatus for automatically sterilizing syringe needles is presented and which may be made available in each hospital room, physician's treatment room or other areas wherein medicinal injections are administered. The heat by which the treatment is achieved, is produced by an electrically heated ceramic tube that quickly conducts and dissipates heat as applied by resistance elements in contact therewith. Following insertion of a needle into the core of the tube, timing means automatically quickly brings the tube temperature up to the range of 900/1000 degrees F., maintains this treatment temperature for a prescribed time and then permits quick cooling of the tube—all within less than 40 seconds and operating with 600 Watts of power. The timer circuits which are provided include signal lights indicating to the user the warmup, treatment and cool-down periods while any malfunction that prevents the heating tube from attaining its proper treatment temperature within a prescribed time automatically signals a fault and precludes further actuation of the heating tube until the situation is remedied.

Accordingly, one of the objects of the present invention is to provide an improved contaminated needle sterilizer including an electrrically heated tube with control and signal means regulating the application of energy to an inserted needle to achieve and maintain a prescribed temperature for a period calculated to destroy existing bioburden.

Another object of the present invention is to provide an improved contaminated needle sterilizer including a heater tube which is electrically heated to elevate the temperature of the air gap within the tube to the range of approximately 900/1000 degrees F. such that a needle inserted therein is sterilized and annealed to prevent the re-use of even the sanitized needle.

A further object of the present invention is to provide an improved contaminated needle sterilizer including an electrically heated tube containing sensing means and which through timed control means achieves, maintains and allows dissipation of an appropriate temperature to accomplish sterilizing and annealing of the needle within less than forty seconds.

Still another object of the present invention is to provide an improved contaminated needle sterilizer including a ceramic heater tube having a central air core dimensioned to freely receive and treat the elongated shaft but not the hub of a hypodermic needle.

With these and other objects in view which will more readily appear as the nature of the invention is better understood, the invention consists in the novel combination and assembly of parts hereinafter more fully described, illustrated and claimed with reference being made to the attached drawings.

BRIEF DESCRIPTION OF THE DRAWINGS

Similar reference characters designate corresponding parts throughout the several figures of the drawings.

DESCRIPTION OF THE PREFERRED EMBODIMENT

Figure 1:
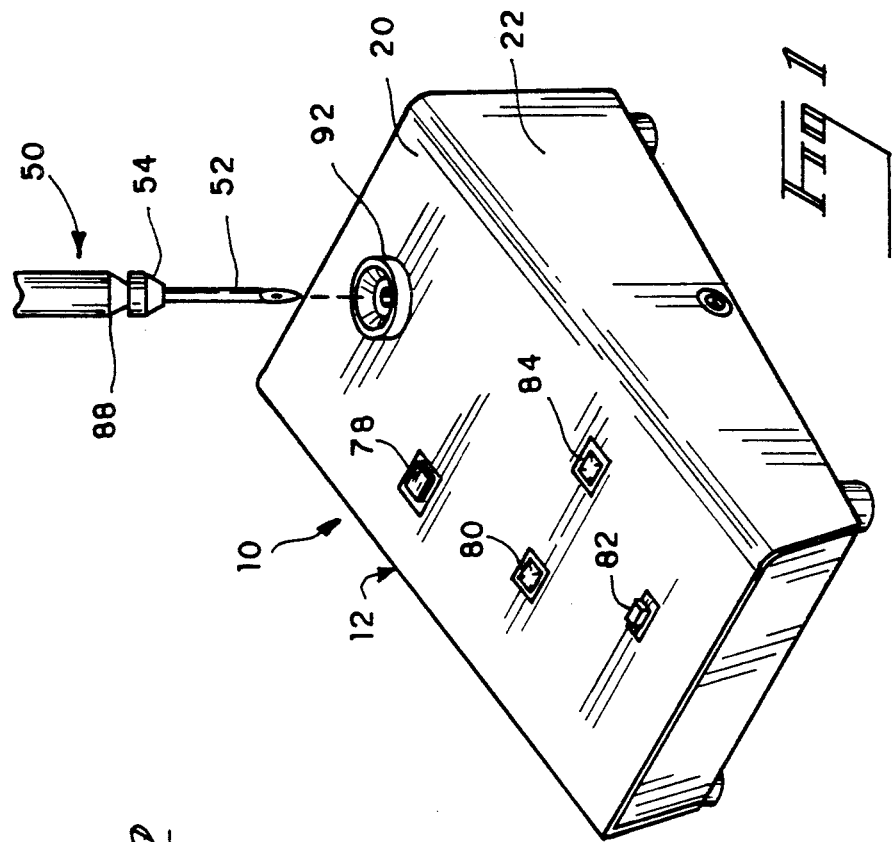
FIG. 1 is a top perspective view of the sterilizer according to the present invention.

Referring now to the drawings, particularly FIG. 1, the present invention will be seen to comprise a contaminated cannula sterilizer generally designated 10 and which includes a relatively compact housing or cabinet 12. The unobtrusiveness and economical aspects of the sterilizer 10 readily adapts it to be disposed upon each patient's bedside table or the like to allow attending medical personnel to immediately safely dispose of any likely contaminated syringe needles following the administration of an injection.

Figure 2:
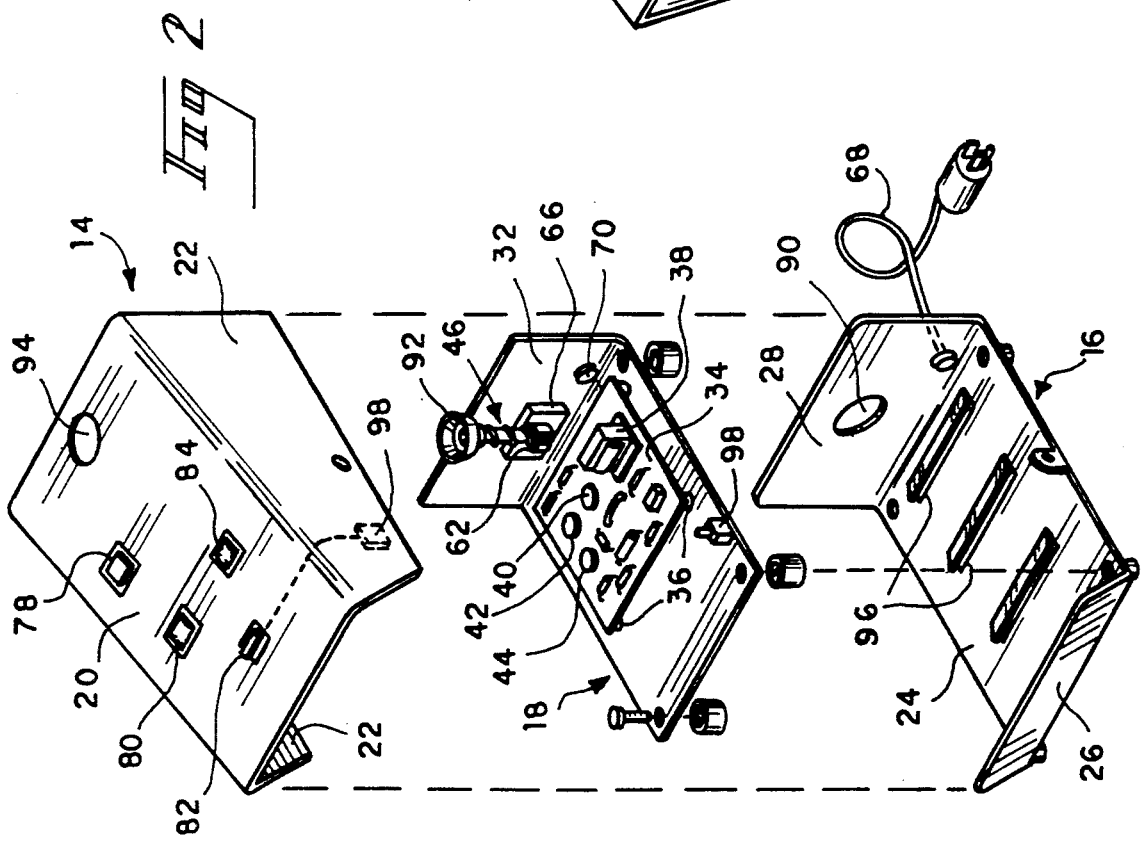
FIG. 2 is an exploded perspective view of the sterilizer of FIG. 1.

As will be seen from FIG. 2 of the drawings, the housing 12 includes a cover member 14 ovelying a lower member 16, within which is contained the component unit 18. The cover member 14 is formed with a top panel 20 from which depend a pair of side walls 22,22 while the lower member 16 includes a base plate 24 having opposite front and rear walls 26 and 28, respectively. With the exception of the operator's controls and system signaling means, the various operating elements of the sterilizer are carried by the component unit 18 which includes a mounting plate 30 having an upstanding rear wall 32.

Various electronic components of the unit are mounted upon a components board 34 suitably removably attached above the plane of the plate 30, as by mounting fixtures 36. These components include a power limiter transformer 38, digital timers 40,42,44 and well known solid state components controlling the sequence of operations as will be described hereinafter.

Figure 3:
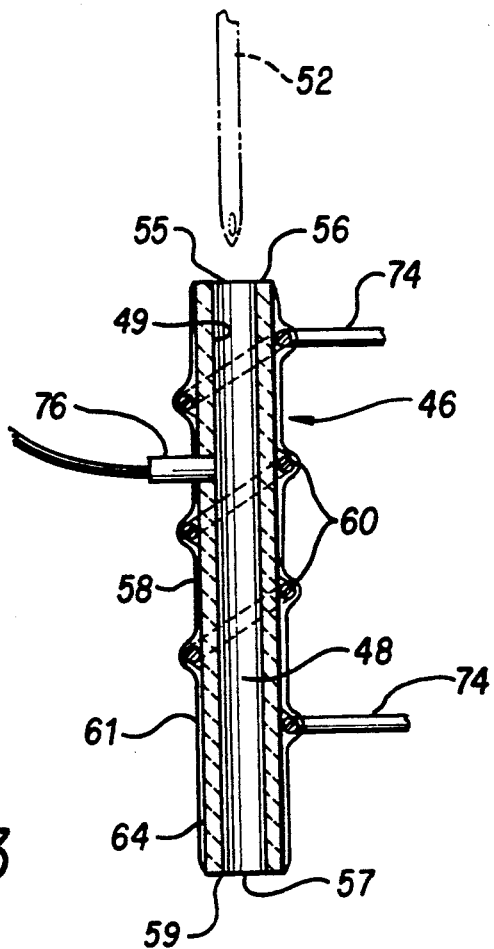
FIG. 3 is an enlarged view of the cannula heating tube of FIG. 2.

The principal working element that accomplishes the sterilization of a contaminated cannula is the needle heating tube 46 which comprises an elongated cylindrical tube of ceramic composition, shown most clearly in FIG. 3. This tube is preferably formed with an O.D. of 0.250 inches and is provided with an axial bore or core 48 as formed by the interior periphery 49 and defining an I.D. of 0.150 inches. With this configuration it will be appreciated that when a user inserts a contaminated syringe assembly 50 with its needle 52 fully disposed within the confines of the tube bore 48, the needle hub 54 will abut the top wall 56 of the heating tube 46 and thus indicate the full and proper insertion of the needle in preparation for treatment by the sterilizer 10.

The tube 46 is adapted to be heated by means of electrical resistance wiring, such as 25 gage nichrome wire and which is helically or otherwise applied about the exterior periphery 58 of the tube body to provide the plurality of spaced apart windings 60 extending substantially throughout its axial extent. An outer layer or coating 61 of ceramic composition overlies and thus encapsulates the windings 60. The wired tube 46 will be seen from FIG. 2 to be fixedly mounted within the component unit 18 by means of a bracket 62 engaging the tube lower end 64 and which is carried by an insulator block 66 attached to the rear wall 32. In this manner it will be seen that the tube is supported in that area which is subject to the least amount of heat and is the first area to become cool when the wires 60 are de-energized. This observation follows since the tube and its bore 48 will register the greatest amount of heat in a progressive manner, from the lower end 64 toward the top wall 56, in view of the natural inclination of heat to rise and also, in the case of the bore 48, due to the accelerated convection as produced by the chimney effect.

Figure 4:
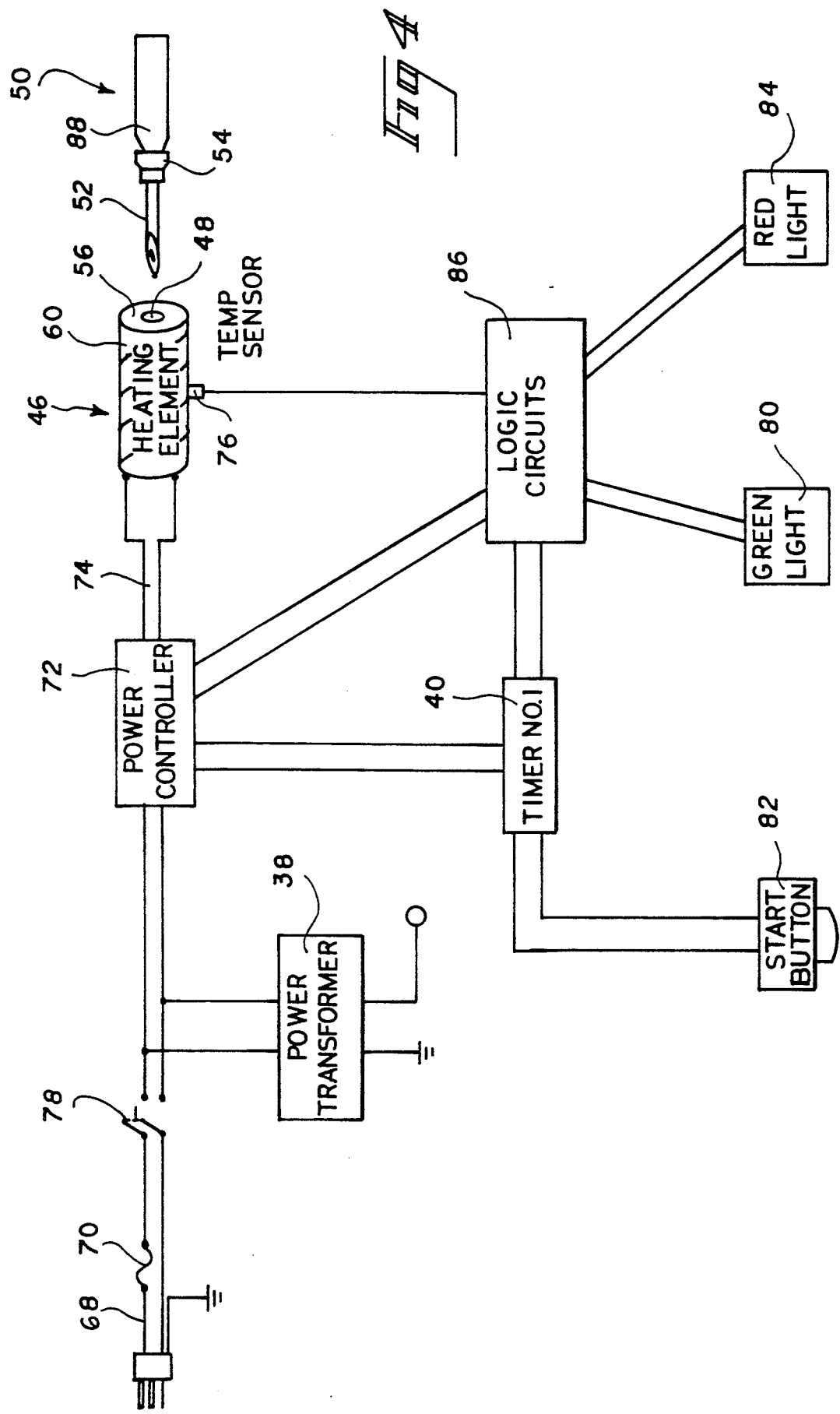
FIG. 4 is a diagrammatic view of the operable components of the invention.

The energy to power the heating tube 46 is supplied by a conventional 110 VAC power cord 68 with the components of the unit being protected from this line voltage by means of a 10 Amp fuse 70. The transformer 38, driven by this incoming voltage, produces the 12 VDC necessary to power the supporting logic circuits, controls and signal devices. As shown in FIG. 4, the protected line voltage is directed to a power controller 72 which controls the passage of electrical current to the tube heating wires 60 by way of the wiring 74 between the controller and tube.

The referenced timing means cooperate with the power controller to insure a positive and efficient operation of the sterilizer 10. Such operation necessitates that a rapid heat-up of the tube 46 occurs with regulation of its heated cycle and with some type of acknowledgement to the user indicating the current status. In this manner the least amount of energy will be consumed to accomplish the stated objective and should the mechanism fail to achieve proper heat-up within a prescribed time, the existence of a possible fault in the system will be announced.

The temperature status of the heating tube 46 is monitored by sensor means comprising a thermocouple 76 radially disposed through the wall of the tube 46 in its medial area. In this manner, the temperature of the heating tube bore 48 may be monitored during use of the apparatus and its signal utilized to control the desired functioning as will be explained hereinafter. To operate and monitor the condition of the sterilizer 10, several components are provided on the top panel 20 of the cover member 14. The user first turns on the power from the line cord 68 by means of a double-pole doublethrow power switch 78 and this 'on' condition will be simultaneously confirmed as a unit-on green light 80 is illuminated. The unit will then be merely in a stand-by mode as no other components thereof are then activated until further action as described below is taken. When a contaminated syringe assembly 50 is to be treated, the user inserts the cannula 52 into the top opening 55 of the heating tube 46 as shown in FIG. 1 and then presses a start button or switch 82. At this time the green ready signal 80 is turned off and a red heat signal or lamp 84 is illuminated. This initiates the first timer 40 which immediately signals the power controller 72 to allow current to pass through the wires 74 to the heating tube 46 and which then begins to heat up.

As the resistance wiring 60 become red hot, the heating tube 46 is rapidly heated and accordingly heats the air within the vertical bore 48 thereof. Since substantially the full height of the tube 46 is wound by the wiring 60, it will be appreciated that the hottest area of the bore 48 will be the upper reaches adjacent the tube top wall 56. This is due to the natural upward convection of heat and which is enhanced by the flue effect generated by the open ended tube 46. The purpose of the first timer 40 is to verify that the proper operating temperature is reached within the tube bore 48 within a prescribed short time, such as within 15 seconds. Thus, if the required operating temperature of between 900–1000 degrees F. is not reached within this limit of the first timer 40, as reported by the thermocouple 76, this timer signals the power controller 72 to interrupt the supply of current through the wiring 74 to the heater. Simultaneously, the red and green signal lamps 84 and 80 enter a flashing cycle to indicate to the user that a possible fault exists. Before re-attempting to operate the apparatus, it is necessary to power down the entire device by removing the power cord 68 from its source of electricity. The user may re-attach the power line cord 68 and press the start switch 82 again and the apparatus will proceed as normal if the prior fault signal was predicated upon a momentary condition. Any permanent fault condition will require inspection and maintenance by an authorized repair facility.

Figure 5:
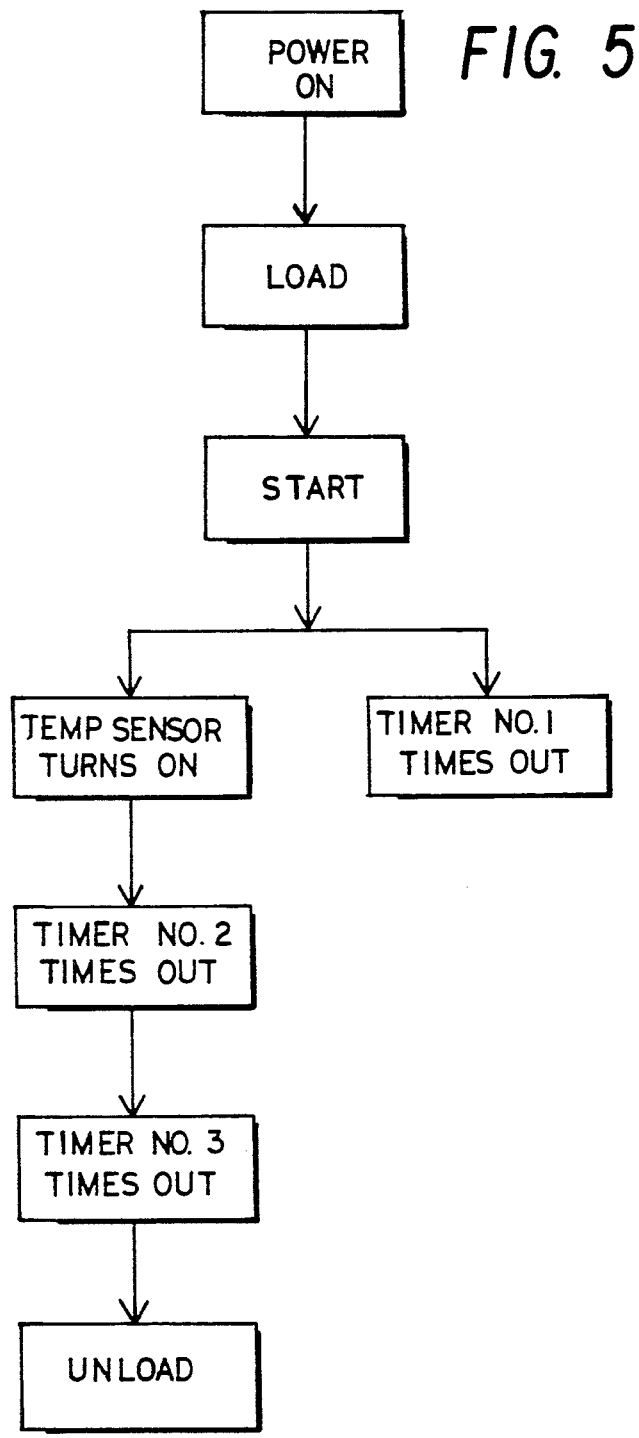
FIG. 5 is a flow chart depicting the sequence of operation of the sterilizer.

Suitable well known logic circuitry 86 on the components board 34 coordinates the operation of the various components of the device as diagrammatically shown in FIG. 4 while the sequence as now being described is represented in the flow chart of FIG. 5.

Under normal operations, the heating tube 46 rapidly attains the prescribed operating temperature of between 900–1000 degrees F. well within the cycle of the first timer 40 and when the sensor 76 signals reaching this level to the logic circuitry 86, the first timer 40 is reset and the second timer 42 is activated. This latter timer maintains the heating of the tube for a prescribed time interval, usually less than the time limit of the first timer 40, by allowing the power controller 72 to continue delivering current through the wiring 74. This period of operation may be referred to as the soak or temperature hold phase as it continues and maintains the required heating of the tube for the period of time necessary for the heated air to act upon the cannula 52 disposed within the upper reaches of the tube bore 48.

Upon the timing out of the second timer 42, the logic circuitry 86 signals the power controller 72 to disconnect current to the heating tube 46 and simultaneously activates the third timer 44. The duration of the third timer is relatively short, say 5 seconds and this period represents the cooldown phase. Upon timing out of the third timer 44, the red signal lamp 84 turns off and the green signal lamp 80 is turned on, while all three timers are reset. The hypodermic syringe with its attached needle 52 may now be removed and safely discarded.

A used needle treated as above will be understood to have been subjected to such an elevated temperature for a sufficient period of time to result in a needle that is decontaminated of known bioburden. The achievement of the referenced temperature, in a dry medium and with consumption of relatively little energy, is possible due to the unique heating tube 46 and wherein the ceramic body thereof is preferably formed with an O.D. of only 0.250 inch and yields an I.D. of but 0.150 inch, thus having a wall thickness of but 0.050 inch or, a ratio of bore to wall thickness of 3:1. With such construction, a minimal mass of the ceramic material must be heated before conduction results in the heating of the air in the vertical bore 48 and then, as this bore is heated, its minimal diameter insures that little energy is wasted on air that does not convey its dry heat to the contained needle.

During the treatment operation, the hub 54 of the inserted needle, having a diameter significantly greater than that of the heating tube bore 48, will be disposed upon the tube top wall 56. This further enhances heat transfer from the bore air to the needle as the hub at least partially closes the otherwise open top end of the heating tube to force an accumulation of the heated air, in the very area containing the needle.

Not only does the instant sterilizer 10 serve to destroy and vaporize bioburden existing in or on the needle 52 itself, but the concentrated application of dry heat will be understood to migrate by conduction throughout the hub body and even to the lower area 88 of the syringe barrel, thereby destroying residual product as previously involved during injection by means of the syringe.

A further benefit of the treatment according to the present process is that the physical state of the decontaminated needle 52 is drastically altered by the heat to which it was subjected. Being exposed to a temperature of 900–1000 degrees F. for the prescribed time interval causes the needle to become annealed, thus effectively rendering illegitimate re-use of the needle impossible. This condition of the needle will also be quite evident visually, in view of its blackened state, thereby further indicating that a needle which has been treated in accordance with the present apparatus is in hand.

The intensity of the above prescribed dry heat treatment may, on rare occasions, serve to detach the treated needle shank 52 from its hub 54 and whereupon the needle will drop down the bore 48 in the tube bottom wall 59. The open bottom 57 of the tube 46 allows for the free passage of such detached needles and thus prevents entrainment of objects within the tube.

The sterilizer 10 as depicted in FIGS. 1 and 2 is configured for disposition upon a horizontal support such as a table top or the like. Alternatively, the unit may be adapted for wall mounting, such as between the two beds in a hospital's double room. In this respect, the heating tube 46 may project through an opening 90 in the rear wall 28 of the lower member 16. This rear wall would then become a top wall and the wall 32 of the component unit would be modified to allow the top wall 56 of the heating tube to be juxtaposed the opening 90. With either this modified arrangement or the originally described configuration, the cover or housing components preferably include a gasket or insulator 92 suitably isolating the top of the heating tube 46 from the surrounding opening 94 in the cover 14.

Other features desirable include air vents or slots 96 provided through the base plate 24 to facilitate cooling of the apparatus and, the provision of a single multi-circuit connector 98 allowing of separation and connection of the plurality of circuits associated with the lamps and switches on the removable cover 14.

It is to be understood that the present invention is not limited to the sole embodiment described above, but encompasses any and all embodiments within the scope of the following claims.

We claim:

1. An apparatus for sterilizing and incapacitating for further use, contaminated needle assemblies including an elongated cannula affixed to an enlarged hub, comprising:
    an elongated heating tube of dielectric composition having opposite open top and bottom walls and defining interior and exterior peripheries, said interior periphery providing an axial central bore within said tube, said tube exterior periphery defining an O.D. of substantially 0.250 inches and said tube interior periphery defining an I.D. of substantially 0.150 inches, said heating tube bore I.D. permitting the entrance of a needle cannula while precluding the entrance of an attached needle hub as the hub abuts said heating tube top wall,
    resistance heating wires encircling said heating tube exterior periphery, a coating of dielectric composition overlying said heating wires,
    power, control and timer means operable to regulate the application of electrical current to said heating wires,
    said control means including means sensing the temperature within said tube bore and operable to permit said heating wires to heat said tube until air within said tube bore reaches a perdetermined level of at least 900 degrees F.,
    said timer means including a first timer monitoring the application of electrical current to said heating wires and interrupting this application of electrical current if the temperature of air within said tube bore has not reached said predetermined level within a prescribed time interval,
    a second timer operable upon attainment of said predetermined temperature within said first timer prescribed time interval to allow continuation of the application of electrical current to said heating wires for a second prescribed time interval representing a heat soak phase,
    separate signal means respectively operable in consonance with the operation of said first and second timers to indicate to a user the status of said timers and thus the application of electrical current to said heating wires, whereby
    with the insertion of a needle cannula into said tube bore with its affixed hub abutting said tube top wall and following expiration of said second prescribed time interval, said cannula is ridden of bioburden, has been annealed and exhibits a blackened appearance clearly indicating its treated condition.

2. The apparatus according to claim 1 wherein, said heating tube comprises a ceramic composition.

3. The apparatus according to claim 1 wherein, said coating comprises a ceramic composition.

4. The apparatus according to claim 1 including,
    a housing providing a lower member cooperating with a cover member,
    a components unit within said housing and having insulation means thereon, and
    bracket means securing said heating tube to said insulation means with said heating tube in a substantially vertical disposition.

5. The apparatus according to claim 1 wherein, said heating tube defines a wall thickness to bore I.D. of substantially 1:3.

6. The apparatus according to claim 1 wherein, said sensing means comprises a thermocouple.

7. The apparatus according to claim 1 wherein, said control means includes logic circuitry, said sensing means connected to said heating tube and delivering an output signal to said logic circuitry, and said logic circuitry regulating said control means in response to said output signal from said sensing means.

8. The apparatus according to claim 7 including, power switch means and start switch means, said power switch means operable to allow electrical current to pass to said logic circuitry, and said start switch means operable to initiate said first timer.

* * * * *